US008778384B2

(12) United States Patent
Harel et al.

(10) Patent No.: US 8,778,384 B2
(45) Date of Patent: Jul. 15, 2014

(54) COMPOSITIONS AND METHODS FOR ENCAPSULATING VACCINES FOR THE ORAL VACCINATION AND BOOSTERING OF FISH AND OTHER ANIMALS

(75) Inventors: Moti Harel, Pikesville, MD (US); Brian Carpenter, Baltimore, MD (US)

(73) Assignee: Advanced Bionutrition Corporation, Columbia, MD (US)

( * ) Notice: Subject to any disclaimer, the term of this patent is extended or adjusted under 35 U.S.C. 154(b) by 0 days.

(21) Appl. No.: 13/466,279

(22) Filed: May 8, 2012

(65) Prior Publication Data

US 2012/0288552 A1 Nov. 15, 2012

Related U.S. Application Data

(63) Continuation-in-part of application No. 13/204,745, filed on Aug. 8, 2011, now Pat. No. 8,329,209, which is a continuation of application No. 12/409,607, filed on Mar. 24, 2009, now Pat. No. 7,998,502.

(60) Provisional application No. 61/487,127, filed on May 17, 2011, provisional application No. 61/038,809, filed on Mar. 24, 2008.

(51) Int. Cl.
*A61K 39/00* (2006.01)
*A61K 39/38* (2006.01)
*A61K 45/00* (2006.01)

(52) U.S. Cl.
USPC ............ 424/442; 424/184.1; 424/278.1; 424/439; 424/450; 424/451

(58) Field of Classification Search
USPC ............ 424/184.1, 439, 450, 451, 489, 490, 424/499, 278.1
See application file for complete search history.

(56) References Cited

U.S. PATENT DOCUMENTS

| | | | |
|---|---|---|---|
| 6,485,950 B1 | 11/2002 | Kumar et al. | |
| 7,670,627 B2 | 3/2010 | Shefer et al. | |
| 7,956,031 B2 | 6/2011 | Naidu et al. | |
| 7,998,502 B2 | 8/2011 | Harel | |
| 2004/0081638 A1 | 4/2004 | Kyle | |
| 2004/0177392 A1 | 9/2004 | Barratt et al. | |
| 2004/0224019 A1 | 11/2004 | Shefer et al. | |
| 2006/0024404 A1 | 2/2006 | Kyle | |
| 2006/0120999 A1 | 6/2006 | Dhar et al. | |
| 2006/0121468 A1 | 6/2006 | Allnut et al. | |
| 2006/0127453 A1 | 6/2006 | Harel | |
| 2006/0130162 A1 | 6/2006 | Kyle et al. | |
| 2007/0082008 A1 | 4/2007 | Harel et al. | |
| 2007/0292952 A1 | 12/2007 | Dhar et al. | |
| 2008/0044481 A1 | 2/2008 | Harel | |
| 2008/0194504 A1 | 8/2008 | Kyle et al. | |
| 2008/0268063 A1 | 10/2008 | Jon et al. | |
| 2009/0181363 A1 | 7/2009 | Dhar | |
| 2009/0238845 A1 | 9/2009 | Harel | |
| 2009/0238890 A1 | 9/2009 | Piechocki et al. | |
| 2009/0246184 A1 | 10/2009 | Harel et al. | |
| 2010/0143481 A1 | 6/2010 | Shenoy et al. | |
| 2011/0293657 A1 | 12/2011 | Harel | |
| 2012/0040010 A1 | 2/2012 | Harel et al. | |

FOREIGN PATENT DOCUMENTS

| | | |
|---|---|---|
| EP | 2105129 | 9/2009 |
| WO | WO 95/31184 | 11/1995 |
| WO | WO 02/41829 | 5/2002 |
| WO | WO 02/076391 | 10/2002 |
| WO | WO 03/086454 | 10/2003 |
| WO | WO 03/089579 | 10/2003 |
| WO | WO 03/103692 | 12/2003 |
| WO | WO 2004/043139 | 5/2004 |
| WO | WO 2004/043140 | 5/2004 |
| WO | WO 2005/017134 | 2/2005 |
| WO | WO 2005/115341 | 12/2005 |
| WO | WO 2006/122299 | 11/2006 |
| WO | WO 2007/058462 | 5/2007 |
| WO | WO 2007/067207 | 6/2007 |
| WO | WO 2007/104562 | 9/2007 |
| WO | WO 2007/117511 | 10/2007 |
| WO | WO 2008/063910 | 5/2008 |
| WO | WO 2008/076975 | 6/2008 |
| WO | WO 2008/140610 | 11/2008 |
| WO | WO 2008/154294 | 12/2008 |
| WO | WO 2010/042555 | 4/2010 |
| WO | WO 2010/111347 | 9/2010 |
| WO | WO 2010/111565 | 9/2010 |
| WO | WO 2012/021783 | 2/2012 |

OTHER PUBLICATIONS

Harel, M. et al. Advanced DHA, EPA, and ArA enrichment materials for marine aquaculture using single cell heterotrophs. Aquaculture, vol. 213, pp. 347-362, 2002.*
Friend, Advanced Drug Delivery Reviews, 2005, 57:247-265.
Benyacoub, B., Rochat, F., K.Y. S.,Rochat, I., Antille, N., Cherbut, C., von der Weid, T., Schiffrin., E.J., Blum, S., 2008. Feeding a Diet Containing a Fructooligosaccharide Mix Can Enhance Salmonella Vaccine Efficacy in Mice. J. Nutr. 138, 123-129.
Dang, J.M., Leong, K.W., 2006. Natural polymers for gene delivery and tissue engineering. Adv. Drug Deliv. Rev. 58(4), 487-499.
Van der Lubben, I.M., Verhoef, J.C., Borchard, G., Junginger, H.E., 2001. Chitosan for mucosal vaccination, Advanced Drug Delivery Reviews 52 (2) 139-144.
van der Lubben, I.M., Verhoef, J.C., van Aelst, A.C., Borchard, G., Junginger, H.E., 2001, Chitosan microparticles for oral vaccination: preparation, characterization and preliminary in vivo uptake studies in murine Peyer's patches. Biomaterials 22(7), 687-694.
Wu, X.S., 2004; Synthesis, characterization, biodegradation, and drug delivery application of biodegradable lactic/glycolic acid polymers: Part III. Drug delivery application Artif. Cells Blood Substit. Immobil Biotechnol 32(4), 575-591.

(Continued)

*Primary Examiner* — Rodney P Swartz
(74) *Attorney, Agent, or Firm* — RatnerPrestia

(57) ABSTRACT

The invention relates to a composition comprising a pharmaceutically active agent and a bioadhesive delivery system that provides for the oral delivery of a vaccine to animals, particularly aquatic animals.

16 Claims, 3 Drawing Sheets

(56) References Cited

OTHER PUBLICATIONS

S. Bravo and PJ Midtlyng (2007) The Use of Fish Vaccines in the Chilean Salmon Industry 1999-2003. Aquaculture 270: 36-42.

Chopra, S., Mahdi, S., Kau, r.J., Iqbal, Z., Talegaonkar, S., F.J, A., 2006. Advances and potential applications of chitosan derivatives as mucoadhesive biomaterials in modern drug delivery. J. Pharm. Pharmacol. 58(8), 1021-1032.

Malik, D.K., Baboota, S., Ahuja, A., Hasan, S., Ali, J., 2007. Recent advances in protein and peptide drug delivery systems. . Curr. Drug Deliv. 4(2), 141-151.

Kim, T.J., Kim, K.H., Lee, J.I., 2007. Stimulation of mucosa and systemic antibody responses against recombinant transferrin-binding protein B of Actinobacillusus pleuropneumoniae with chitosan after tracheal administration in piglets. J. Vet. Med. Sci. 69(5), 535-539.

Kang, M.L., Jiang, H.L., Kang, S.G., Guo, D.D., Lee, D.Y., Cho, C.S., Yoo, H.S., 2007 Pluronic F127 enhances the effect as an adjuvant of chitosan microspheres in the intranasal delivery of Bordetella bronchiseptica antigens containing dermonecrotoxin. Vaccine 25(23), 4602-4610.

Davis, S.S., 2006, The use of soluble polymers and polymer microparticles to provide improved vaccine responses after parenteral and mucosal delivery. Vaccine 24(2), 7-10.

Siwicki, A.K. et al. “Dietary intake of immunostimulants by rainbow trout affects non-specific immunity and protection against furunculosis.” Veterinary Immunology and Immunopathology, vol. 41, No. 1-2, May 1, 1994, pp. 125-139.

Yin, Y. et al. “Preparation and evaluation of lectin-conjugated PLGA nanoparticles for oral delivery of thymopentin,” Journal of Controlled Release 116 (2006) 337-345.

Sayin, B. et al. “Chitosan and its derivatives for mucosal immunization.” Current Research and Development on Chitosan in Biomaterials Science, 2008, vol. 1: 143-163.

Tobar et al., Oral Vaccination of Atlantic Salmon Salmo salar against Salmonid rickettsial septicaemia (SRS), abstract, World Aquaculture Society’s 2008 annual international conference (May 19-23, 2008).

Tobar et al., Oral Vaccination of Atlantic Salmon Salmo salar against Salmon Rickettsial Septicaemia, presentation, World Aquaculture Society’s 2008 annual international conference (May 19-23, 2008).

* cited by examiner

COMPOSITIONS AND METHODS FOR ENCAPSULATING VACCINES FOR THE ORAL VACCINATION AND BOOSTERING OF FISH AND OTHER ANIMALS

CROSS-REFERENCE TO RELATED APPLICATION

The present application claims priority to U.S. Provisional Application No. 61/487,127 filed on May 17, 2011 and is also a continuation-in-part application of and claims priority to U.S. patent application Ser. No. 13/204,745 filed on Aug. 8, 2011, now issued as U.S. Pat. No. 8,329,209, which is a continuation application of and claims priority to U.S. patent application Ser. No. 12/409,607 filed on Mar. 24, 2009, now U.S. Pat. No. 7,998,502, which in turn claims priority to U.S. Provisional Application No. 61/038,809 filed in the United States Patent and Trademark Office on Mar. 24, 2008, the contents of which are hereby incorporated by reference herein for all purposes.

BACKGROUND OF THE INVENTION

1. Field of the Invention

The present invention relates to a composition comprising a pharmaceutically active agent, such as, but not limited to, an immunogenic agent (e.g., a vaccine), and a bioadhesive delivery system, that allows the oral administration and delivery of the pharmaceutically active agent essentially unaltered to the intestinal mucosa.

2. Background of Related Art

Orally delivered pharmaceutically active agents present a significant problem in transiting an animal's stomach, an organ whose contents represent a harsh digestive environment consisting of low pH and enzymes specifically designed to denature proteins. As a consequence, orally delivered bacterin or subunit vaccines have not been proven to be efficacious since the antigens are generally modified by the stomach prior to presentation to the immuno-responsive cells of the gut mucosa. A number of approaches have been tested to provide an oral delivery vehicle that would transit the stomach but most have been unsuccessful at the commercial scale. One approach involves the transient changing of the stomach pH, neutralizing gastric enzymes and stimulating the mucosal immune response.

In 2003 about 200 million fish were vaccinated in Chile, primarily for Yersiniosis, Salmonid Ricketsial Septicaemia (SRS), and Infectious Pancreatic Necrosis (IPN) (Bravo, 2007). Of the more than 20 vaccines for aquacultured fish brought to the Chilean market from 1999-2003, none was an orally delivered vaccine.

SRS is a pathology of salmonid fish caused by the intracellular bacterium Piscrickettsia salmonis and is a major infectious disease in the Chilean salmon industry with annual losses exceeding 20%. Unlike other bacterial diseases, the anti-SRS vaccination is not as effective in preventing the disease or in reducing the need for post-infection medication. This is because of a gradual diminishing of the SRS immunogenicity in the vaccinated fish. Boosting the antibody titer in the blood by vaccinating at a later stage should allow the continued protection of the animals throughout the entire commercial growing period. However, it is extremely difficult and economically impractical to provide parenteral vaccine boosters to large animals in the grow-out net pens.

Almost all existing vaccines are delivered to aquatic animals by injection, which is traumatic, inconvenient, time consuming, expensive, has a number of side effects, and may fail to induce an appropriate immunogenic response in mucosal tissues. Thus, a method and system for delivery that avoids these disadvantages would be of great value.

Perhaps the most well known antigen delivery systems are those derived from the linear polymeric esters of lactic acid and glycolic acid (i.e., poly DL-lactide-co-glycolide, PLGA, reviewed by Wu (Wu, 2004). In such systems, immunogenic subunit vaccine components have been captured in polyacrylate and poly-glycolide/lactide beads or liposome-like vesicles through processes utilizing volatile organic solvents such as dichloromethane or chloroform. The solvents are used to form emulsions of polymer solutions or dried lipid films. Encapsulation of antigens into PLGA microcapsules affords a number of advantages including rapid degradation by hydrolysis and subsequent penetration of the Peyer's Patches (concentrated sites of lymphocytic tissue in the intestinal mucosa of higher vertebrates but not in fish). A major disadvantage of PLGA microcapsules is the requisite use of organic solvents. Contact with organic solvents can inactivate or reduce the efficacy of the vaccine by altering the immunogenicity of surface proteins critical to induction of humoral or cellular immune responses. Additionally, poly-acrylate and poly-glycolide/lactide processes typically result in microbeads with extremely low immunogen or antigen capture efficiency.

Polymer microspheres and lamellar particles (e.g., liposomes) have been employed for the improved parenteral and mucosal administration of antigens. Because vaccines themselves may not be efficiently recognized and taken up by mucosal lymphocytes, they typically need to be co-administered with penetration enhancers or adjuvants. Different classes of polymer mixtures are known for potential use as Mucoadhesives (Malik et al., 2007). These include synthetic polymers such as poly (acrylic acid) (PAA), hydroxypropyl methylcellulose and poly(methylacrylate) derivatives, as well as naturally occurring polymers such as hyaluronic acid and chitosan.

Chitosan and various chitosan derivatives have been used for a variety of applications as a biomaterial for tissue engineering, wound healing, and as an excipient for drug delivery (Chopra et al., 2006; Dang and Leong, 2006). Chitosan has occasionally been tested as an adjuvant for mucosal application (Kim et al., 2007), but it is typically applied directly to a mucosal surface such as intranasal application in order to obtain IgA response in the nasopharyngeal mucosa of terrestrial animals (Kang et al., 2007). However, the use of chitosan and various chitosan derivatives in vaccine delivery remains very limited due to poor physicochemical characteristics such as a high transition temperature and interfacial free energy, resulting in a suboptimal interaction with mucosal surfaces and loose interpenetration and interdiffusion of the polymer. This problem is further compounded when used for poikilothermic lower vertebrates like salmonid fish. Chitosan also has the additional disadvantage of a low mechanical strength and solubility.

Thus, there remains a need for effective systems and processes for microencapsulation of immunogenic substances with polymers having superior adhesive and cohesive properties.

SUMMARY OF THE INVENTION

The present invention overcomes the shortcomings of the above-discussed encapsulation systems, wherein the present invention discloses a composition designed for an oral delivery of a primary and or booster vaccination that can be used for animals housed not only in a hatchery but also in grow-out pens. The exceptional mucoadhesive properties of compositions of the present invention provide a successful method of transmucosal drug delivery, especially for lower vertebrates with less developed digestive systems and no Peyer's Patches, such as fish.

One aspect of the present invention provides for a method of producing a bioadhesive delivery vehicle for vaccination of animals, such as aquatic animals, wherein the delivery vehicle is in a form of dry microparticles comprising an immunogenic agent embedded or impregnated in a composite matrix of cross-linked chitosan, and at least one oligosaccharide or short chain polysaccharide. Any applicable oligosaccharides or short chain polysaccharides may be used in the composition. Common short chain polysaccharides include maltodextrins and cyclodextrins. The oligosaccharides may include fructo-oligosaccharides (FOS), galacto-oligosaccharides (GOS) or inulin. Additionally, the dry microparticles include and selected from the group consisting of a beta glucan, squalene, and squalane.

In one embodiment, the composition comprises or consists of at least one pharmaceutically active agent in an amount from about 0.05% to about 10% w/w of composition, at least one bio-adhesive polymer in an amount from about 0.05% to about 10% w/w of composition, at least one short chain polysaccharide or oligosaccharide in an amount from about 0.05% to about 30% w/w of composition and at least one adjuvant selected from the group consisting of a beta glucan, squalene, and squalane in an amount from about 0.1% to about 20% w/w of composition.

In one particular embodiment of the invention, the method comprises producing a bioadhesive delivery vehicle containing an SRS vaccine for use in salmonid fish.

Another aspect of the present invention provides for a feeding regime wherein animals are fed a standard feed containing a bioadhesive delivery vehicle comprising a cationic polysaccharide, in combination with a pharmaceutically active agent, for the oral vaccination of animals. In a particular embodiment, the vaccinated animal is a fish.

Another aspect of the present invention provides for a method of preparing a composition for oral delivery of a pharmaceutically active agent comprising:
  a. preparing an acidic aqueous solution comprising at least one bioadhesive polymer, wherein the bioadhesive polymer is chitosan and the acidic solution has a pH low enough to solubilize the chitosan;
  b. combining an oligosaccharide/short chain polysaccharide selected from the group consisting of inulin, maltodextrin and cyclodextrin into the solution with the solubilized chitosan to form an oligosaccharide/short chain polysaccharide-chitosan solution;
  c. introducing a sugar/emulsifier complex into the oligosaccharide/short chain polysaccharide-chitosan solution to form a smooth emulsion while maintaining the acidic pH of the solution;
  d. combining or emulsifying the pharmaceutically active agent with an adjuvant selected from the group consisting of beta-glucan, shark liver oil and squalane in a solution;
  e. adding the solution of pharmaceutically active agent and the adjuvant into the smooth bioadhesive emulsion;
  f. forming microparticles, beads or hydrogel by precipitating the emulsion into a cross-linking solution; and
  g. drying the microparticles, beads or hydrogel by any conventional means.

The dried microparticles may be further milled to obtain particle size lower than 500 micron.

Preferably, the crosslinking solution comprises from about 1% to about 20% of phosphate or carbonate anions. The crosslinking solution may further comprise about 1% to 30% of a sugar and/or alcohol.

Other aspects and advantages of the invention will be more fully apparent from the ensuing disclosure and appended claims.

DETAILED DESCRIPTION OF THE INVENTION

Definitions

Figure 1:
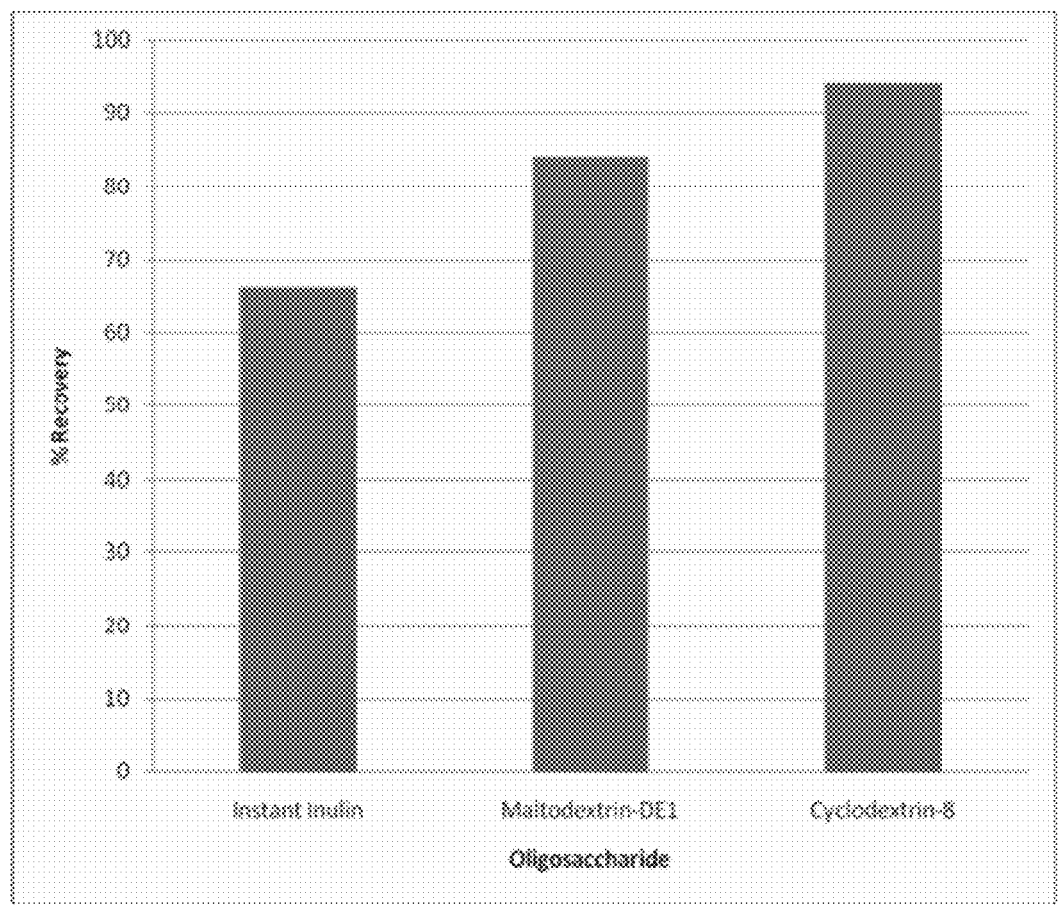
FIG. 1 shows the percentage of dry material that was recovered from the various oligosaccharide formulations after cross-linking and drying.

In describing the present invention, the following terminology is used in accordance with the definitions set out below.

A "pharmaceutically active agent" is defined as any biological material that results in the prevention, cure, or mitigation of a disease in any animal. All vaccines are intended to be included in this definition of pharmaceutically active agents.

An "immunogen" or an "immunogenic agent" is defined as a substance or a composition of matter, which is capable of mounting a specific immune response in an animal. Immunogenic agents would include immunogenic peptides and proteins including mixtures comprising immunogenic peptides and/or proteins; intact inactive, attenuated, and infectious viral particles; intact killed, attenuated, and infectious prokaryotes (e.g., bacterins); intact killed, attenuated, and infectious protozoans including any life cycle stage thereof, and intact killed, attenuated, and infectious multicellular pathogens, recombinant subunit vaccines, and recombinant vectors to deliver and express genes encoding immunogenic proteins (e.g., DNA vaccines).

"Vaccination" is defined as a process that results in a specific immune response generated by an animal against an immunogen or an immunogenic agent.

A "bioadhesive delivery system" is defined as a composition that results in the delivery of an immunogen or an immunogenic agent to the desired location in the gut associated lymphoid tissue (GALT) of the intestinal mucosa.

A "mucoadhesive" molecule is a component of a bioadhesive delivery system that specifically binds to mucosal tissues. Such molecules include, but are not limited to chitosan, hyaluronic acid, gum Karaya, and cationic guar.

DETAILED DESCRIPTION OF THE INVENTION

The present invention provides an improved immunogenic substance for oral delivery. The invention is based on the discovery of unexpected synergetic properties of a complex mixture of chitosan and a short chain polysaccharides such as fructo-oligosaccharide.

Fructans or fructosans are oligosaccharides or short chain polysaccharides comprising a sequence of anhydrofructose units optionally combined with one or more different saccharide residues of the fructose. Fructans can be linear or branched. Fructans can be products obtained directly from a plant or microbial source or else products with a chain length which has been modified (increased or reduced) by splitting, synthesis or hydrolysis, in particular of the enzymatic variety. Fructans generally have a degree of polymerization from 2 to approximately 1000 and preferably from 3 to approximately 60.

The short chain polysaccharide or oligosaccharide is preferably used in an amount of between 0.01 and 30% by weight with respect to the total weight of the composition. More preferably, this amount is between 0.05 and 15% by weight with respect to the total weight of the composition and more preferably between 1 and 10% by weight.

The preferred short chain polysaccharides are inulins, maltodextrins or cyclodextrins. Inulins refer to a group of naturally-occurring fructose-containing oligosaccharides. Because inulin fiber is resistant to digestion in the upper gastrointestinal tract (i.e., the stomach), it reaches the large intestine essentially intact, where it can be digested by indigenous bacteria. Inulins generally consist of chains of polyfructose in which the fructose units are connected to each other mostly or exclusively by β-(2-1) linkages. Inulin occurs in nature, in general, as a polydisperse mixture of polyfructose chains, most of which terminate in one glucosyl unit. They are derived from the roots of chicory (Cichoriumintybus), the dahlia and Jerusalem artichokes. Additionally, inulin can be obtained from bacterial syntheses or can be made in vitro by enzymatic synthesis starting from sucrose. It has been shown that inulin stimulates mucosal immunity and seems to improve efficacy of a Salmonella vaccine in mice (Benyacoub et al., 2008). Although the mechanism of action is unclear, several studies have proposed that inulin may induce changes in colonic epithelium by stimulating proliferation in the crypts, increasing the concentration of polyamines, changing the profile of mucins, and/or modulating endocrine as well as immune functions (Roberfroid, 2005). Inulins also stimulate the growth of Bifidobacterium species in the large intestine. The average degree of polymerization of inulins marketed as nutritional supplements is 10 to 12.

Maltodextrin refers to a group of short chain polysaccharide (complex) carbohydrates, which are defined as a repeating unit of a simple sugar (like glucose or dextrose). Maltodextrin is derived from a natural starch by either exposing to acid or enzymes to partially digest and break down the starch into smaller polymers.

Cyclodextrins (CDs) refer to a family of cyclic oligosaccharides. CDs derive their system of nomenclature from the number of glucose residues in their structure, such that the glucose hexamer is referred to as α-CD, the heptamer as β-CD and the octomer as χ-CD.

These short chain polysaccharides serve in the composition of the present invention as multi-functional drug carriers, through the formation of inclusion complex or the formation of carbohydrate/vaccine conjugate and, thereby potentially enhancing the vaccine bioavailability Chitosan is a linear cationic polysaccharide which is gelled or crosslinked in the presence of anions, such as citrate, phosphate or sulfate. Chitosan has also been shown to possess useful properties such as non-toxicity, high biocompatibility and non-antigenicity. While chitosan is itself largely insoluble in water, solubility markedly increases if the pH is shifted towards the acid condition. To obtain an appreciable polymer concentration, it is therefore necessary to prepare the solution or dispersion with simultaneous use of an acid. To be able to more easily remove this acid from the composition later, it turned out that the acid should have a low boiling point, namely preferably maximally 140° C., in particular maximally 120° C., especially preferred maximally 100° C., and most preferably maximally 80° C., such as hydrogen chloride, hydrogen bromide, trifluoroacetic acid, formic acid and acetic acid. Other suitable acids have the ability to form a lower-boiling binary azeotrope with water, such as acetic acid or propionic acid.

Chitosan can be obtained through the deacetylation of chitin, the major compound of exoskeletons in crustaceans. Chitosan [a-(1~4)-2-amino-2-deoxy-β-D-glucan], a mucopolysaccharide closely related to cellulose, exhibits chemical properties that are determined by the molecular weight, degree of deacetylation, and viscosity. Chitosan can form microparticles and nanoparticles that can encapsulate large amounts of antigens (van der Lubben et al., 2001; Davis, 2006). In the acidic environment of the stomach, chitosan retains its positive charges that hold the particle together. It has been shown that ovalbumin loaded chitosan microparticles can be taken up by the Peyer's Patches of the gut associated lymphoid tissue of higher vertebrates. Additionally, after co-administering chitosan with antigens in nasal vaccination studies in a strong enhancement of both mucosal and systemic immune responses in mice was observed (van der Lubben et al., 2001).

A general method for preparing the compositions for delivery to the gut mucosa is discussed below. Generally, an aqueous solution, suspension or emulsion of a pharmaceutically active agent (e.g., an immunogenic agent, including, but not limited to vaccines) and, if desired, an adjuvant including, but not limited to, beta glucan, lipopolysaccharide, aluminium salts, virosomes and/or squalene. Squalene, or its saturated form, squalane, is a hydrocarbon natural oil primarily produced from shark liver oil or a plant oil such as olive oil. In the animal body, squalene plays a vital role in the synthesis of cholesterol, steroid hormones, and vitamin D. β-Glucans (beta-glucans) are polysaccharides of D-glucose monomers linked by β-glycosidic bonds. β-Glucans are a diverse group of molecules that can vary with respect to molecular mass, solubility, viscosity, and three-dimensional configuration. They occur most commonly as cellulose in plants, the bran of cereal grains, the cell wall of baker's yeast, certain fungi, mushrooms and bacteria.

The vaccine/adjuvant complex is dissolved or suspended in an aqueous solution of a suitable mucoadhesive polymer such as, but not limited to, chitosan and a suitable short chain polysaccharide or oligosaccharide such as, but not limited to, inulin, maltodextrin, cyclodextrin. The resulting solution/suspension is then dispersed directly or by atomization into an aqueous cross-linking solution containing water-soluble phosphate salts. Upon contact, a salt exchange reaction (cross-linking) takes place, resulting in the formation of beads or capsules in which the pharmaceutically active agent is retained. The resulting suspension of microparticles or beads containing the encased pharmaceutically active agent is then collected, dried, and milled if necessary to form particles having a size range from 10-1000 micron. Details of the preparation are set out in the series of steps described below:

Step (a): Preparation of complex mucoadhesive hydrogel. A mucoadhesive polymer such as chitosan, at a concentration of 1 to 10% (w/w), is dispersed in 0.1-5N acetic acid solution at a temperature range of 20 to 65° C. until all polymer granules are fully dissolved. Preferably, the chitosan is at least 85% deacetylated. Additionally it is preferred that the pH of the acidic aqueous solution is from about 2 to about 5. The gelatinization of the polymer granules is required in order to prepare a microparticle possessing the immunogenic property.

In embodiments of the invention, short chain polysaccharide components are also added at a concentration of from about 1 to 30% (w/w) to improve protection of the antigen from stomach acidity, bile acids and proteases and increase the intestinal adsorption and bioavailability of the antigen. Examples of applicable materials include, but not limited to, chitosan oligosaccharide (COS), inulin, fructo-oligosaccharides (FOS), and various dextrins, such as maltodextrins and cyclodextrins. These absorption-increasing components may dissolve more readily in intestinal juices than other matrix materials. Consequently, permeability and biodegradability of the matrix polymer can be increased, resulting in an improved release of the pharmaceutically active agent at the desired location in the GALT of the intestinal mucosa.

Step (b): Complex formation of the mucoadhesive material and a short chain polysaccharide or oligosaccharide. Without wishing to be bound by theory, it is believed that the processes described herein yield a novel complex composition mediated by an emulsifier/sugar complex and comprising polysaccharides and oligosaccharides in the form of a complex matrix having an insoluble microparticle nature. Generally, the emulsifiers can be, but are not limited to, any of monoglycerides, sorbitan esters, propylene glycol esters, lecithin, polysorbates and sucrose esters of medium and long chain saturated fatty acids, and the sugars will be any mono- or disaccharides such as, but not limited to glucose, fructose, or sucrose. A solution comprising an emulsifier/sugar mediating mixture (containing 0.5 to 12.5% w/w emulsifier and 5-30% w/w sugar) is added to the mucoadhesive polysaccharide and short chain polysaccharide or oligosaccharide solution at a temperature range of from 20 to 65° C. and pH 3-5 until a smooth and stable emulsion has formed. This emulsion is stabilized by the interaction between positive charge of the cationic polysaccharide, the emulsifier and hydroxyl groups of the short chain polysaccharides or oligosaccharides. The increased hydrophobicity and elasticity of the mucoadhesive polysaccharide and emulsifier helps delay or prevent penetration of water or gastric juices into the matrix once formed into microparticles.

Step (c): Addition of immunogenic substance. A solution comprising a pharmaceutically active agent, such as, but not limited to, an immunogen or immunogenic antigen is mixed with an adjuvant such as beta-glucan or emulsified with squalene oil, in an amount of about 0.1% to 10% (w/w) by weight of the composition and more preferably from about 1% to 4%, and then mixed in the mucoadhesive solution described in Step (b) above.

Step (d) Cross-linking reaction. The slurry can be dried to produce a powder by a number of art-recognized methods including, but not limited to, low temperature spray drying, belt drying, freeze drying, drum drying or flash drying. In a preferred embodiment, the slurry is extruded through a tube or needle ranging from 10 um to 1,000 um in diameter to fall dropwise or in a continuous stream into a cross-linked solution containing 1-15% sodium triphosphate (TPP) in 1-30% alcohol in water solution. Alternatively, the slurry can be spray-atomized into an alcohol/aqueous solution containing 1-10% sodium triphosphate. Wet particles can be harvested from the cross-linking bath by any suitable means well known in the art (e.g., filtration, centrifugation, etc) and mixed with any acceptable thickening agent such as methylcellulose, pectin, alginate, xanthan gum, carboxymethyl cellulose, hydroxypropyl cellulose, and the like, and sprayed onto feed pellets (i.e., top-coated). Alternatively, the wet particles can be dried using conventional processes well known in the art such as, but not limited to, vacuum drying, freeze drying, spray drying, and tunnel drying, milled to the appropriate size class if necessary, and then mixed with fish oil or other edible oils prior to application to a standard commercially available feed by top-coating using methods known in the art.

In one embodiment the slurry is mixed with sucrose before the drying process and/or extruding process and cross-linked in 1-15% w/w TPP+1-30% w/w sugar in 1-30% w/w alcohol in water solution followed by drying.

Feeding strategy for oral vaccination: Fish having a mature immune system (for Atlantic Salmon generally at about 0.5 g) are ready to be orally vaccinated. However the instant invention provides a flexible strategy that also allows the vaccination of, or boosting the immunogenic response of larger fish and other animals. To effectively induce the immunogenic response, the fish or other animals should be orally fed in a single event at a similar or greater dose of immunogen that is usually provided by injection or immersion. To maximize the fish immunogenicity and depending the on the immunogen type, fish size and responsiveness, this single feeding event may be repeated (e.g., every three days for up to ten feeding events).

EXAMPLES

Example 1

Production of a bioadhesive delivery system containing egg ovalbumin antigen. High DE chitosan (>80%, Sigma, St. Louis, Mo.), (3 gram) was dissolved in 100 ml of 0.5N acetic acid at 50° C. Twenty (20) gram Instant Inulin (Cargil, Minneapolis, Minn.) or twenty (20) gram maltodextrin DE1 or twenty (20) gram cyclodextrin were added to make an acidic slurry. Three (3) gram soy lecithin (Archer-Daniels-Midland Co., Decatur, Ill.) were added to the acidic slurry and allowed to complex under continuous mixing with the chitosan solution for 30 min. The pH of the acidic complex slurry was then adjusted to 5.8 with sodium hydroxide and the slurry allowed to cool down to room temperature. A 10 ml solution containing 100 mg egg ovalbumin and 100 mg beta glucan (Sigma) was admixed in the slurry and the slurry extruded through 21G needle into a 50 ml solution containing 10% w/w sodium triphosphate, 40% w/w sucrose and 20% isopropanol to form hydrogel strings. After about 2 hours of hardening in the cross linking solution, the firm hydrogel strings were harvested, freeze-dried over night and milled to a particle size below 200 microns. FIG. 1 shows the percentage of dry material that was recovered after cross-linking and drying of the various short chain polysaccharides or oligosaccharides formulations. It shows that cyclodextrin was captured the most (94%) within the cross-linked chitosan polymers as compared with inulin (66%) or maltodextrin DE1 (84%).

Example 2

Figure 2:
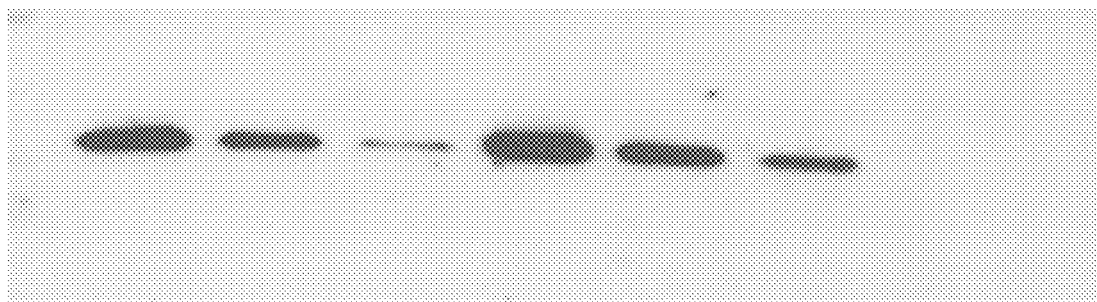
FIG. 2 shows the Western blot detection of SRS antigen in chitosan slurry and after freeze drying and milling. Lane 1:4 ng SRS in chitosan slurry; Lane 2:2 ng SRS in chitosan slurry; Lane 3:1 ng SRS in chitosan slurry; Lane 4, 5, 6 are the respective SRS amounts in freeze dried and milled chitosan matrix.

Production of Bioadhesive Particles containing Salmonid Rickettsial Septicaemia (SRS) Vaccine. Complex slurry at pH 5.8 (100 ml) was prepared as described in Example 1. Ten (10) ml solution containing attenuated SRS vaccine ($5 \times 10^{11}$/ml SRS killed bacteria) without adjuvant (commercially available from the vaccine manufacturer) was mixed with 100 mg beta glucan and mixed in the chitosan solution. The slurry was then extruded into 50 ml cross linking solution as described in Example 1. The hydrogel strings were allowed to harden for 3 hour and then harvested from the solution and freeze-dried over night and milled to a particle size below 200 microns. FIG. 2 depicts a Western blot gel chromatography analysis showing the recovery of various amounts of SRS antigen from a freeze dried chitosan powder relative to its amount in the chitosan slurry before freeze drying. The analysis demonstrates that the antigen retained its immunogenicity and activity within the chitosan matrix and was not affected by the encapsulation process.

Example 3

Figure 3:
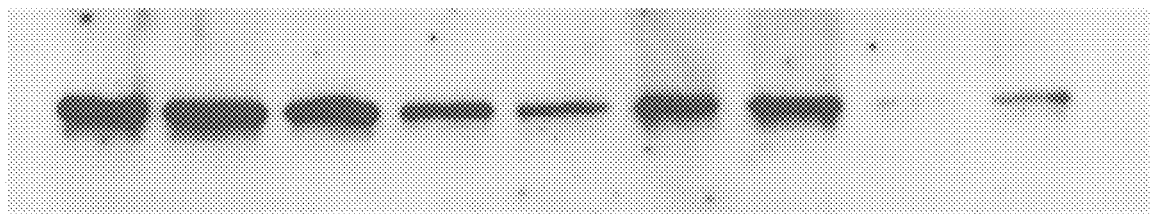
FIG. 3 shows the Western blot analysis showing the recovery of the antigen in fish feed. Lanes 1-5 are several dilutions of the antigen in buffer, Lanes 6-9 are the respective dilutions of fish feed containing a similar amount of antigen.

Animal feed containing Immunogenic Microparticles for oral delivery. Fifteen (15) grams of dry immunogenic microparticles prepared as in Example 1 and 2 were mixed with 30 g of fish oil. The oily mixture is sprayed on 1 kg of standard commercial feed for animal including fish, livestock, and chicken or companion animal. FIG. 3 depicts a Western blot gel chromatography analysis showing the recovery of the antigen from fish feed relative to a similar amount in PBS buffer. The analysis demonstrates that the antigen retained its immunogenicity and activity throughout the encapsulation process and coating on fish feed.

Example 4

Oral Vaccination of Atlantic Salmon Using the Immunogenic Microparticles of the Present Invention. Atlantic salmon juveniles ca. 10 g size are stocked at 30 kg/m$^3$ of fresh water and at temperature of 12° C. Water quality is maintained by rapidly exchanging the tank water through mechanical and biofiltration systems. Fish are fed 4 times daily a total ration of 2% body weight on a commercial feed. Every 3 days the diet is replaced with a 2% vaccine top-coated diet as described in Example 3 for a period up to 30 days. Elevated antibodies titer against the orally delivered vaccine is measured in the fish blood serum over the subsequent four months.

Example 5

Production of Bioadhesive Particles containing Infectious salmon anemia (USA) Vaccine. Infectious salmon anemia (USA) is an orthomyxoviral disease that has had devastating effects on farmed Atlantic salmon. Fish feed containing ISA immunogenic microparticles was produced as described in Example 1 and 3. Complex slurry at pH 5.8 (100 ml) containing cyclodextrin (short chain polysaccharide or oligosaccharide) was prepared as described in Example 1. Eight (8) ml solution containing recombinant ISAV vaccine (commercially available from the vaccine manufacturer) was emulsified with 10 ml of squalene and 2 ml of Span-80 using Ultra-Torax homogenizer at 15,000 RPM and the emulsion mixed in the chitosan solution using low speed hand mixer at 1000 RPM). The slurry was then extruded into 50 ml cross linking solution as described in example 1. The hydrogel strings were allowed to harden for 3 hour and then harvested from the solution and freeze-dried over night and milled to a particle size bellow 200 microns.

Example 6

Bivalent Oral Vaccination of Atlantic Salmon against SRS and ISAV using top-coated feed with Immunogenic Microparticles of the Present Invention. Atlantic salmon juveniles ca. 10 g size are raised as described in Example 4. Fish are fed 4 times daily a total ration of 2% body weight on a commercial feed. Every three (3) days, for a period up to 30 days, the diet is replaced with top-coated feed containing 2% SRS vaccine and 2% ISAV vaccine as described in Example 3 and 5, respectively. Elevated titers of antibodies against the orally delivered bivalent vaccines are measured in the fish blood serum over the subsequent four months.

REFERENCES

The contents of all references cited herein are incorporated by reference herein for all purposes.

Benyacoub, B., Rochat, F., K. Y, S., Rochat, I., Antille, N., Cherbut, C., von der Weid, T., Schiffrin., E. J., Blum, S., 2008. Feeding a Diet Containing a Fructooligosaccharide Mix Can Enhance Salmonella Vaccine Efficacy in Mice. J. Nutr. 138, 123-129.

Chopra, S., Mandi, S., Kau, r. J., Iqbal, Z., Talegaonkar, S., F. J, A., 2006. Advances and potential applications of chitosan derivatives as mucoadhesive biomaterials in modern drug delivery. J. Pharm. Pharmacol. 58(8), 1021-1032.

Dang, J. M., Leong, K. W., 2006. Natural polymers for gene delivery and tissue engineering. Adv. Drug Deliv. Rev. 58(4), 487-499.

Davis, S. S., 2006. The use of soluble polymers and polymer microparticles to provide improved vaccine responses after parenteral and mucosal delivery. Vaccine 24(2), 7-10.

Kang, M. L., Jiang, H. L., Kang, S. G., Guo, D. D., Lee, D. Y., Cho, C. S., Yoo, H. S., 2007. Pluronic F127 enhances the effect as an adjuvant of chitosan microspheres in the intranasal delivery of Bordetellabronchiseptica antigens containing dermonecrotoxin. Vaccine 25(23), 4602-4610.

Kim, T. J., Kim, K. H., Lee, J. I., 2007. Stimulation of mucosal and systemic antibody responses against recombinant transferrin-binding protein B of Actinobacilluspleuropneumoniae with chitosan after tracheal administration in piglets. J. Vet. Med. Sci. 69(5), 535-539.

Malik, D. K., Baboota, S., Ahuja, A., Hasan, S., Ali, J., 2007. Recent advances in protein and peptide drug delivery systems. Curr. Drug Deliv. 4(2), 141-151.

Roberfroid, M. B., 2005. Introducing inulin-type fructans. Br J. Nutr. 93, 13-25.

van der Lubben, I. M., Verhoef, J. C., Borchard, G., Junginger, H. E., 2001. Chitosan for mucosal vaccination. Advanced Drug Delivery Reviews 52 (2), 139-144.

van der Lubben, I. M., Verhoef, J. C., van Aelst, A. C., Borchard, G., Junginger, H. E., 2001. Chitosan microparticles for oral vaccination: preparation, characterization and preliminary in vivo uptake studies in murine Peyer's patches. Biomaterials 22(7), 687-694.

Wu, X. S., 2004. Synthesis, characterization, biodegradation, and drug delivery application of biodegradable lactic/glycolic acid polymers: Part III. Drug delivery application Artif. Cells Blood Substit. Immobil. Biotechnol 32(4), 575-591.

S. Bravo and P J Midtlyng (2007) The Use of Fish Vaccines in the Chilean Salmon Industry 1999-2003. Aquaculture 270: 36-42

That which is claimed is:

1. A composition for oral delivery, comprising one or more pharmaceutically active agents constituting in total from about 0.05% to about 10% w/w of the composition, one or more bio-adhesive polymers selected from the group consisting of chitosan, dimethyl chitosan, trimethyl chitosan, carboxymethyl chitosan and mixtures thereof and constituting in total from about 0.05% to about 10% w/w of the composition, and one or more short chain polysaccharides or oligosaccharides constituting in total from about 0.05% to about 30% w/w of the composition, wherein the composition is a crosslinked solid;

wherein said one or more pharmaceutically active agents are selected from the group consisting of immunogenic peptides, immunogenic proteins, intact inactive viral particles, attenuated viral particles, infectious viral particles, intact killed prokaryotes, attenuated prokaryotes, infectious prokaryotes, intact killed protozoans, attenuated protozoans, infectious protozoans, intact killed multicellular pathogens, attenuated multicellular pathogens, infectious multicellular pathogens, recombinant subunit vaccines, recombinant vectors encoding immunogenic proteins, recombinant vectors for delivering and expressing genes encoding immunogenic proteins, and mixtures of any of these, and wherein the composition further comprises one or more adjuvant compounds.

2. The composition of claim 1, wherein the one or more adjuvant compounds are selected from the group consisting of beta-glucans, squalene, and squalane, and are present in total in an amount from about 0.1% to about 20% w/w based on the weight of the composition.

3. The composition of claim 1, wherein said one or more short chain polysaccharides or oligosaccharides are selected from the group consisting of inulins, maltodextrins, cyclodextrins and mixtures thereof.

4. A method of preparing the composition according to claim 1, comprising:
(i) preparing an acidic aqueous solution comprising at least one bioadhesive polymer, wherein the bioadhesive polymer is chitosan and the acidic aqueous solution has a pH low enough to gelatinize the chitosan;
(ii) combining a short chain polysaccharide or oligosaccharide into the acidic aqueous solution;
(iii) combining the pharmaceutically active agent with an adjuvant selected from the group consisting of beta-glucan, squalene and squalane oil in a solution or a water in oil emulsion;
(iv) adding the solution or emulsion of step (iii) into the product of step (ii); and
(v) precipitating or extruding the product of step (iv) into a cross-linking solution comprising a crosslinking agent to form a solid product.

5. The method of claim 4, wherein the short chain polysaccharide or oligosaccharide is selected from inulin, maltodextrins and cyclodextrins.

6. The method of claim 4, wherein the composition comprises from about 0.1% to about 10% of the adjuvant compound.

7. The method of claim 4, wherein the adjuvant compound is selected from beta-glucans.

8. The method of claim 4, wherein in step (iii) the pharmaceutical agent is in said water in oil emulsion.

9. The method of claim 4, wherein the crosslinking agent comprises from about 1% to about 20% of phosphate or carbonate anions.

10. The method of claim 4, wherein the crosslinking solution further comprises about 1% to 30% of a sugar.

11. The method of claim 4, wherein the crosslinking solution further comprises about 1% to 30% of an alcohol.

12. The composition according to claim 1, wherein the crosslinked solid is combined with a thickening agent selected from the group consisting of methylcellulose, pectin, alginate, xanthan gum, carboxymethyl cellulose and hydroxypropyl cellulose.

13. The composition according to claim 12, further comprising feed pellets upon which the composition is topcoated.

14. The composition according to claim 1, produced by a method comprising
(i) preparing an acidic aqueous solution comprising at least one bioadhesive polymer, wherein the bioadhesive polymer is chitosan and the acidic aqueous solution has a pH low enough to gelatinize the chitosan;
(ii) combining a short chain polysaccharide or oligosaccharide into the acidic aqueous solution;
(iii) combining the pharmaceutically active agent with an adjuvant selected from the group consisting of beta-glucan, squalene and squalane oil in a solution or a water in oil emulsion;
(iv) adding the solution or emulsion of step (iii) into the product of step (ii); and
(v) precipitating or extruding the product of step (iv) into a cross-linking solution comprising a crosslinking agent to form a solid product;
wherein in step (iii) the pharmaceutically active agent is in said water in oil emulsion.

15. A method of orally vaccinating or boosting an animal against a pathogen, comprising the steps of:
dispersing or spraying a liquid mixture comprising the composition of claim 14 and a liquid carrier onto an animal feed; and
delivering the resulting animal feed to the animal at a similar or greater dose of immunogenic agent than is usually provided by injection or immersion.

16. The method of claim 15, wherein the delivery is repeated every three days for up to ten feeding events to maximize immunogenicity